United States Patent [19]

Swift

[11] 4,200,800
[45] Apr. 29, 1980

[54] REDUCED DOSE CT SCANNING

[75] Inventor: Roderick D. Swift, Belmont, Mass.

[73] Assignee: American Science & Engineering, Inc., Cambridge, Mass.

[21] Appl. No.: 848,144

[22] Filed: Nov. 3, 1977

[51] Int. Cl.² ............................................. G03B 41/16
[52] U.S. Cl. .................................. 250/445 T; 250/514
[58] Field of Search ................... 250/445 T, 505, 511, 250/512, 513, 514

[56] References Cited

U.S. PATENT DOCUMENTS

| | | | |
|---|---|---|---|
| 3,881,110 | 4/1975 | Hounsfield | 250/445 T |
| 3,922,552 | 11/1975 | Ledley | 250/445 T |
| 4,045,672 | 8/1977 | Watanabe | 250/445 T |
| 4,057,725 | 11/1977 | Wagner | 250/445 T |
| 4,075,489 | 2/1978 | Neal | 250/445 T |
| 4,097,747 | 6/1978 | Kowalski | 250/445 T |

Primary Examiner—Craig E. Church
Attorney, Agent, or Firm—Cushman, Darby & Cushman

[57] ABSTRACT

A CT scanner having a rotating X-ray source and a stationary circular array of 600 contiguous detectors includes a sliding shutter mechanism incorporated in the precollimator system that prevents detectors at the beginning and at the end of a scan from receiving radiation while progressively increasing and decreasing, respectively, the current to the X-ray tube.

20 Claims, 7 Drawing Figures

REDUCED DOSE CT SCANNING

BACKGROUND OF THE INVENTION

The present invention relates in general to CT scanning and more particularly concerns novel apparatus and techniques for reducing dosage to a patient without sacrifice in image quality.

The commercially available CT scanner from American Science and Engineering, Inc. comprises a circular array of 600 contiguous detectors illuminated in sequence by a rotating X-ray source that emits a fan beam. Those detectors within the arc of the fan beam at any instant of time during a scan are "active" and are periodically sampled to provide X-ray transmission data. The array of data associated with a given detector during a scan is called a "detector fan" or "data fan". It is important that each detector fan be obtained smoothly and continuously in time without significant interruption between adjacent samples or rays. Furthermore, it is important to have the data obtained at the beginning and at the end of the scan blend smoothly together. Compliance with these two criteria avoids discontinuities within individual fans and between spatially adjacent fans obtained at the beginning and at the end of the scan that would result in artifacts in the reconstructed CT image.

To achieve both smoothness and continuity in time, it is preferred to scan somewhat in excess of 360° and to select suitable parts of the totality of data thus obtained as explained in greater detail below. A disadvantage of this approach is that some detectors are thus illuminated twice, providing some data which obeys the smoothness and continuity criteria, and additional data which is discarded because it violates the criteria. The unused data represents wasted dose to the patient.

It is an important object of the invention to provide an improved CT scanner.

It is another object of the invention to achieve the preceding object while reducing the dosage to which a patient is subject.

It is a further object of the invention to achieve one or more of the preceding objects without sacrifice in the quality of the reconstructed CT image.

It is still a further object of the invention to achieve one or more of the preceding objects with relatively little additional structure that is relatively inexpensive, reliable and relatively easy to incorporate into a CT scanner having a stationary array of detectors.

SUMMARY OF THE INVENTION

According to the invention, in a CT scanner having a stationary circular array, there is means for relatively angularly displacing a source of penetrating radiant energy and the array of detectors over a path resulting in the source ordinarily illuminating the same group of detectors both at the beginning and at the end of a scan cycle and means for restricting the emission of radiant energy at the beginning and at the end of a scan cycle to reduce the number of detectors that are illuminated with penetrating radiant energy twice in a scan cycle. Preferably, the latter means comprises shutter means to limit the field of the penetrating radiant energy radiating from the source. The shutter means may comprise a rectangular slot in a plate having intermittent sliding motion relative to the source or a parallelogram-shaped opening in a plate moving continuously or intermittently perpendicular to the plane of the fan beam. A further form comprises a slot in a curved plate which achieves its correct position relative to the source by rotation about the scan axis. Still another form the invention may take comprises separate plates, independently driven, to obscure the fan beam from either edge of the scan as required according to the invention. Another feature of the invention resides in progressively increasing and decreasing X-ray tube current at the beginning and end of a scan cycle, respectively, to provide part of the desired weighting.

Numerous other features, objects and advantages of the invention will become apparent from the following specification when read in connection with the accompanying drawing in which:

DETAILED DESCRIPTION OF PREFERRED EMBODIMENTS

Figure 1:
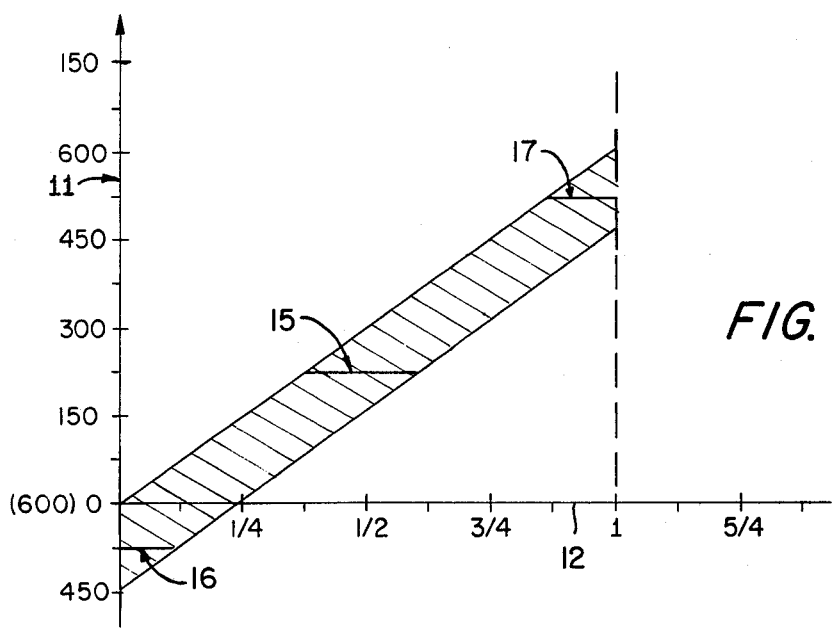
FIG. 1 is a graphical representation of detectors illuminated as a function of scan cycle showing the data available in a circular scan of exactly one revolution.

With reference now to the drawing and more particularly FIG. 1 thereof, there is shown a graphical representation of numbered data fans as a function of source position for a fan beam that embraces 150 of the 600 detectors. The data fan number, modulo 600, is plotted along the ordinate 11. The abscissa 12 represents the fractional revolutions of the scan cycle or source rotation. The shaded parallelogram bounds the domain of active detectors, and illustrates the data available within a 360° scan without regard to the smoothness criteria. The interception of the active domain by horizontal lines from a given detector number shows the portion of the scan during which that detector fan is obtained. Data fans 0–450 are obtained without interruption in time, as for example the data fan 15 of detector number 225, which is obtained during the region of ⅜ to ⅝ revolution of the scan cycle. Data fans of detectors 451–599 are separated in time, as exemplified by detector fan 525 which is broken into part 16 obtained at the beginning of a scan and part 17 obtained at the end of a scan.

Figure 2:
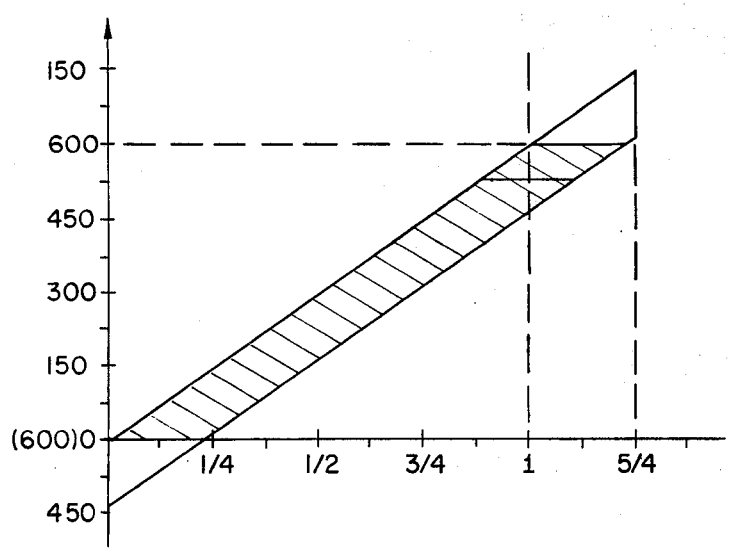
FIG. 2 is a graphical representation as in FIG. 1 showing the scan extended by a quarter revolution for removing discontinuities.

Referring to FIG. 2, there is shown a graphical representation of the scan extended to 5/4 revolutions and sufficient so that detector fans 451–599 may be obtained continuously in time to remove discontinuities within detector fans. The parallelogram bounds the region of active detectors, but only the data fans in the shaded region, which represents a complete set of 600 data fans, are obtained continuously in time. There remains a temporal discontinuity between spatially contiguous detector fans 0 and 599, obtained at the beginning and end of the scan, respectively.

Figure 3:
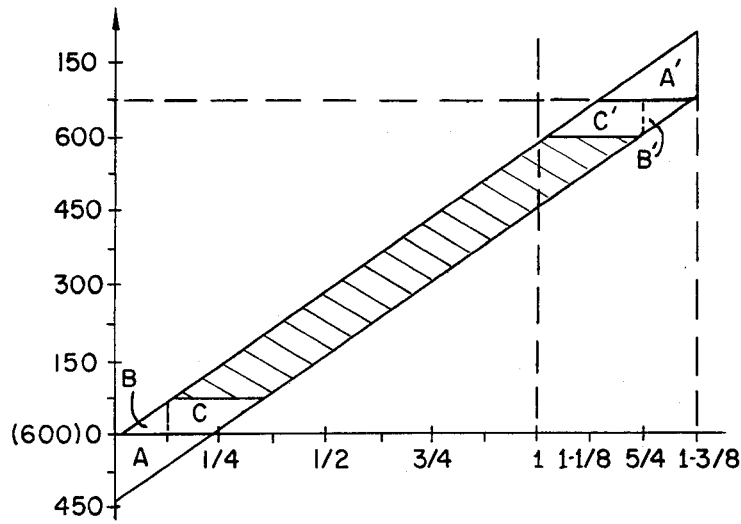
FIG. 3 is a graphical representation as in FIGS. 1 and 2 showing extending the scan even further for eliminating the temporal discontinuity between spatially contiguous detector fans 599 and 0 obtained at the beginning and end of the scan.

Referring to FIG. 3, there is shown the scan extended still further to 1⅜ revolution to remove the latter discontinuity and obtain the first 75 detector fans a second time. Weighted averages of these 75 redundant data fans are used in the CT image reconstruction by gradually increasing the weights of the leading group to full value and gradually reducing the weight of the trailing group to zero. The net effect is to blend together data at the extremes of the scan and thereby smooth out any discontinuities in the reconstructed image.

To achieve the desired information for producing a reconstructed image of high quality essentially free of artifacts requires the scan cycle indicated in FIG. 3. Yet, the information in portions A and A' is not used in reconstructing the image. According to the invention, means are provided for blocking radiation of the designated detectors in regions A and A' to significantly reduce the dosage received by a patient.

Figure 4:
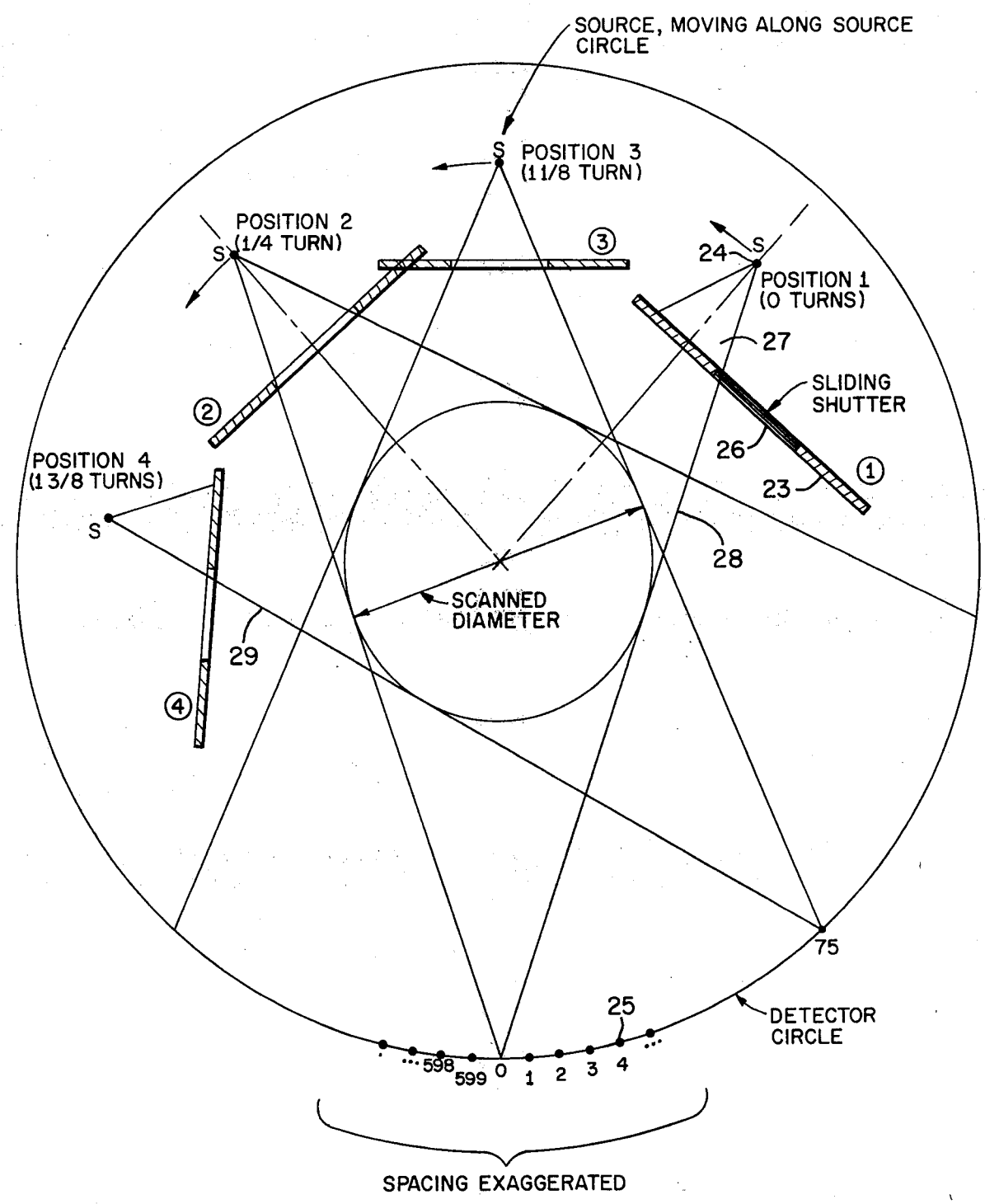
FIG. 4 is a diagrammatic representation of a shuttered aperture as a function of source position to reduce dosage according to the invention.

Referring to FIG. 4, there is shown a diagrammatic representation of a system for eliminating radiation in the direction of the detectors corresponding to regions A and A' in FIG. 3. A sliding shutter in the precollimator effectively narrows the fan beam at the beginning and end of a scan cycle so that it only illuminates those detectors providing useful data. Throughout the mid-portion of the cycle, all active detectors are illuminated. The apparatus comprises X-ray source 24 that starts from position 1 and advances counterclockwise during a complete scan through position 2 at a quarter turn to position 3 at 1⅛ turns and finally to position 4 at 1⅜ turns. Shutter 23 comprises a lead plate formed with an aperture 26 corresponding substantially to the width of fan beam 27 while the portions on either side of slot 26 are greater than the width of fan beam 27. At the beginning of the scan with source 24 in position 1, shutter 23 is positioned to allow only the initial edge 28 of fan beam 27 to pass through aperture 26 and illuminate detector 0 while obscuring detectors 451–599. As source 24 progresses counterclockwise, shutter 23 also slides progressively counterclockwise relative to source 24 to continue to illuminate detector 0 while continuing to obscure the detectors clockwise of detector 0. As shutter 23 advances, aperture 26 transmits an ever widening sector of the fan beam 27 to illuminate detectors 1, 2, 3 et seq. At position 2 a quarter turn into the scan, the full width of fan beam 27 passes through aperture 26 to illuminate detectors 0–149. Shutter 23 then remains in a stationary position relative to source 24 until the scan has advanced to position 3 at 1⅛ turns into the scan, where source 24 illuminates detectors 526 to 75. Thereafter, shutter 23 again advances progressively counterclockwise relative to source 24 to prevent illumination of all detectors counterclockwise of detector 75. When source 24 reaches position 4 at the end of the scan (1⅜ turns) it illuminates only detector 75 at the final edge 29 of the fan beam 27.

Figure 5:
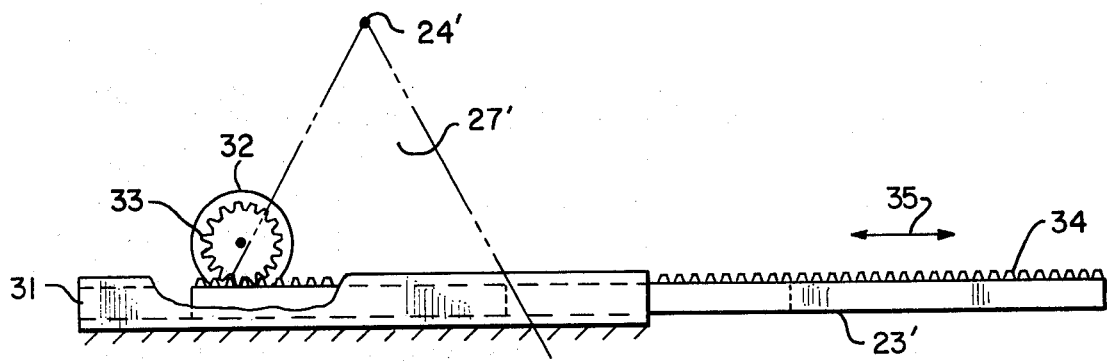
FIGS. 5 and 6 are elevation and plan views, respectively, of a preferred form of sliding shutter mechanism.
Figure 6:
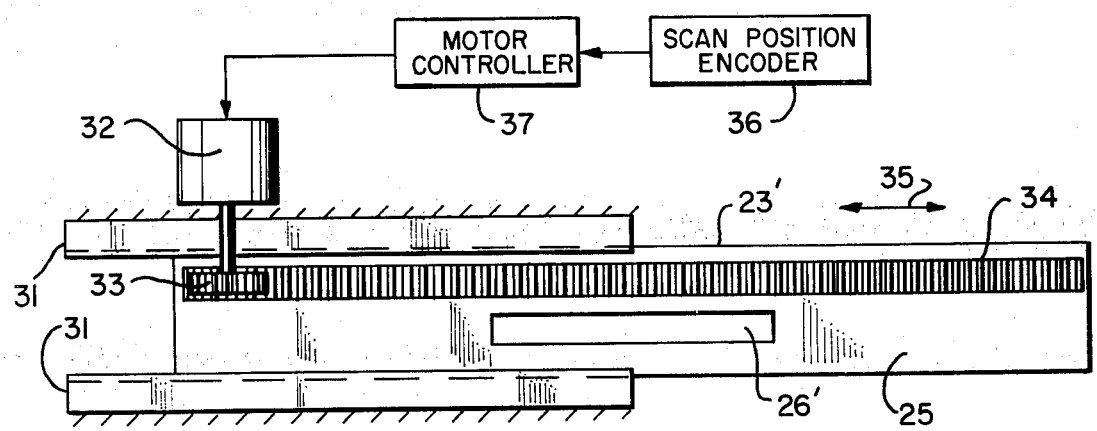

FIGS. 5 and 6 are elevation and plan views, respectively, of the preferred embodiment of a sliding shutter mechanism, wherein 23' is a shutter assembly comprising X-ray opaque plate 25 containing aperture 26' and having rack gear 34 firmly attached. Shutter assembly 23' is supported and guided by stationary tracks 31 such that it is constrained to move only in the direction of arrows 35 by the action of stepper motor 32 and pinion gear 33 on rack gear 34. FIGS. 5 and 6 illustrate the initial position of the sliding shutter mechanism, for which the relative position of the X-ray source 24' and X-ray fan beam 27' are shown schematically in FIG. 5. Synchronization of the motion of the sliding shutter mechanism with the scan cycle of FIGS. 3 and 4 is achieved by a scan position encoder 36 providing positional information to motor controller 37 which in turn controls the incremental stepping of motor 32 by techniques well-known in the art. Upon completion of a scan cycle, motor controller 37 resets the sliding shutter mechanism to its initial position.

Other techniques well-known in the art may be used for controlling the shutter to source relationship diagrammatically represented in FIG. 4. For example, the relative displacement between shutter and X-ray source could be effected by a mechanical linkage actuated when the source is within the designated regions. Alternatively, transducing means may be provided to sense the position of shutter 23 and provide a control signal that controls the shutter 23 as indicated in FIG. 4. Still another embodiment might comprise a slot in a curved plate which rotates about the scan axis in synchronism with the source 24 to establish the correct aperture opening. Still another embodiment might comprise a parallelogram-shaped opening in an X-ray opaque plate which is moved perpendicular to the fan beam either continuously or intermittently depending on the dimensions of the opening to establish the correct fan beam aperture in synchronism with the motion of source 24. Still another embodiment might comprise separate X-ray opaque plates independently driven to obscure the fan beam from either edge in accordance with the techniques described in connection with FIG. 4.

Still another approach may comprise a servo system which senses the outputs of detectors 599 and 0 from position 1 to position 2 and the output of detectors 75 and 76 from position 3 to position 4 of FIG. 4. In the first region the controller progressively advances the shutter clockwise so that detector 0 is illuminated while detector 599 is obscured and in the second region positions the shutter so that detector 75 is illuminated while detector 76 is obscured. The specific servo techniques for establishing these relationships are well-known in the art.

With reference again to FIG. 3, regions B and C at the beginning of a scan cycle and B' and C' at the end of a scan cycle represent repeated data fans from the same group of 75 detectors (detectors 0–74), which are suitably weighted to remove the effects of discontinuities between the two ends of the scan cycle. According to the invention, means are provided to reduce by half the dose which would otherwise be incurred during portions B and B' of the scan, without sacrificing the quality of the reconstructed CT image. To this end, weighting is accomplished by controlling the X-ray tube current to progressively increase over the first ⅛ rotation of the source corresponding to region B and to progressively decrease over the last ⅛ rotation of the source corresponding to region B'. A further advantage of this approach is that the X-ray tube uses less power during the ends of the scan, resulting in a significant reduction of the order of 5 to 10% of the X-ray tube thermal load.

Again referring to FIG. 3, the dose and X-ray tube thermal load can be further reduced, with only a slight sacrifice of quality in the reconstructed CT image, by extending the progressively increasing and decreasing current ramps into or across regions C and C', respectively.

Figure 7:
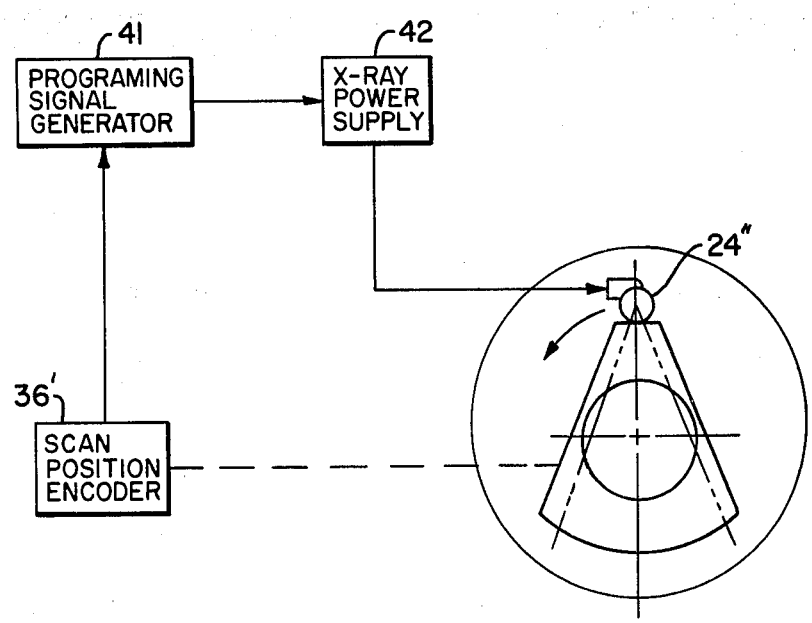
FIG. 7 is a block diagram illustrating the logical arrangement of a system for achieving current control in synchronism with the scan cycle.

FIG. 7 shows a block diagram illustrating the logical arrangement to achieve current control in synchronism with the scan cycle by techniques well-known in the art. Encoder 36' generates signals indicating the angular position of X-ray source 24" in the scan cycle. This positional information is used by programming signal generator 41 to produce a programming signal proportional to the desired X-ray tube current sequence, in turn causing power supply 42 to supply to X-ray source 24" a current having the desired amplitude and temporal characteristics.

There has been described novel apparatus and techniques for significantly reducing the dosage to a patient without sacrifice of image quality and further reducing power dissipated and thermal load. It is evident that those skilled in the art may now make numerous other departures from and modifications of the specific embodiments described herein without departing from the inventive concepts. Consequently, the invention is to be construed as embracing each and every novel feature and novel combination of features present in or possessed by the apparatus and techniques herein disclosed.

What is claimed is:

1. In a CT scanner having a fixed circular array of contiguous detectors extending about substantially the entire circumference of a circular path and a source of a fan beam of penetrating radiant energy relatively movable with respect to the detectors about an axis in a region to be scanned within said circular path, the improvement comprising,
   means for passing a substantially constant width of said fan beam during substantially one complete revolution of said source and for variably limiting the width of said fan beam along the direction of scan only at end portions of a complete scan cycle comprising substantially more than one complete revolution of said source so that the number of detectors illuminated near each end point of the complete scan cycle is proportional to the distance between the source and each end point.

2. The improvement in accordance with claim 1 wherein said means for passing and for limiting comprises shutter means.

3. The improvement in accordance with claim 1 and further comprising means for establishing the intensity of said penetrating radiation proportional to the distance between said source and a respective end scan point for a predetermined end portion of said path of relative movement.

4. The improvement in accordance with claim 3 wherein said means for passing and for limiting the width comprises shutter means.

5. The improvement in accordance with claim 3 wherein said source of penetrating radiant energy comprises an X-ray tube and said means for reducing radiation comprises means for controlling the magnitude of the X-ray tube current so that it is inversely proportional to the distance between said source and a respective end point.

6. The improvement in accordance with claim 1 wherein the rotational scan is at least 5/4 revolutions.

7. The improvement in accordance with claim 1 wherein said means for limiting permits, at each end point of the scan, the illumination of substantially only one detector.

8. The improvement in accordance with claim 1 wherein said means for limiting comprises a sliding shutter of material opaque to said penetrating radiant energy formed with an aperture transparent thereto that is relatively movable with respect to said source and said detectors for progressively reducing the width of said fan beam along the direction of scan at end portions thereof so that the number of detectors illuminated near each end point of the scan is proportional to the distance between the source and each end point while passing substantially the full beam width between said end portions.

9. The improvement in accordance with claim 8 wherein said aperture corresponds substantially to said full beam width along the path of relative motion.

10. The improvement in accordance with claim 9 wherein said means for limiting comprises a driving motor coupled to said shutter,
    and means for controlling operation of said motor in accordance with the scan position to alter the width of said fan beam along the direction of scan at end portions of said scan so that the number of detectors illuminated near each end point of the scan is proportional to the distance between the source and each end point while the full width of said fan beam illuminates said detectors between said end portions.

11. A CT scanner comprising:
    a fixed circular array of plural radiation detectors extending about substantially the entire circumference of a circular path, said detectors being disposed substantially within a plane and directed inwardly about the region to be scanned;
    a fan-beam radiation source inwardly directed about an axis within said region to be scanned, said source providing a fan-shaped beam of penetrating radiation directed substantially within said plane through said region, rotatable about said axis and capable of simultaneously illuminating a group of said detectors; and
    beam limiting means disposed in the path of said fan-shaped beam for controllably passing into said region a substantially constant width of said fan beam during substantially one complete revolution of said source and a variable portion of said fan-shaped beam as a predetermined function of the rotational position of said beam only at end portions of a complete scan cycle comprising substantially more than one complete revolution of said source.

12. A CT scanner as in claim 11 further comprising beam intensity control means connected to vary the intensity of said fan-shaped beam as a predetermined function of the rotational position of said beam only at said end points of a complete scan cycle.

13. A CT scanner as in claim 11 wherein:
    said source causes said fan-shaped beam to rotate from a start point to an end point during a scanning cycle;
    said beam limiting means passes an increasing portion of said fan-shaped beam as it moves away from said start point; and
    said beam limiting means passes a decreasing portion of said fan-shaped beam as it moves toward said end point.

14. A CT scanner as in claim 13 further comprising beam intensity control means connected to vary the intensity of said fan-shaped beam as a predetermined function of the rotational position of said beam.

15. A CT scanner as in claim 14 wherein said beam intensity control means increases the intensity of said beam as it moves away from said start point and decreases the intensity of said beam as it moves toward said end point.

16. A CT scanner as in claim 15 wherein said beam limiting means and said beam intensity control means provide a substantially constant intensity and a substantially constant shape of the beam passing through said region throughout substantially one complete revolution of the beam.

17. A CT scanner comprising:
a fixed array of plural radiation detectors disposed substantially within a plane and directed inwardly about the region to be scanned;
a fan-beam radiation source inwardly directed about an axis within said region to be scanned, said source providing a fan-shaped beam of penetrating radiation directed substantially within said plane through said region, rotatable about said axis and capable of simultaneously illuminating a group of said detectors;
beam limiting means disposed in the path of said fan-shaped beam for controllably passing into said region a variable portion of said fan-shaped beam as a predetermined function of the rotational position of said beam at the beginning and end portions of a complete scanning cycle of more than one revolution; and
beam intensity control means connected to vary the intensity of said fan-shaped beam as a predetermined function of the rotational position of said beam simultaneously with the operation of said beam limiting means.

18. A CT scanner as in claim 17 wherein:
said source causes said fan-shaped beam to rotate from a start point to an end point during a scanning cycle;
said beam limiting means passes an increasing portion of said fan-shaped beam as it moves away from said start point; and
said beam limiting means passes a decreasing portion of said fan-shaped beam as it moves toward said end point.

19. A CT scanner as in claim 18 wherein said beam intensity control means increases the intensity of said beam as it moves away from said start point and decreases the intensity of said beam as it moves toward said end point.

20. A CT scanner as in claim 19 wherein said beam limiting means and said beam intensity control means provide a substantially constant intensity and a substantially constant shape of the beam passing through said region throughout substantially one complete revolution of the beam.

* * * * *

UNITED STATES PATENT AND TRADEMARK OFFICE
CERTIFICATE OF CORRECTION

PATENT NO. : 4,200,800
DATED : April 29, 1980
INVENTOR(S) : Roderick D. Swift

It is certified that error appears in the above—identified patent and that said Letters Patent is hereby corrected as shown below:

Column 5, line 60, delete "inversely".

Column 7, line 15, "fized" should read -- fixed --.

Signed and Sealed this

Eighth Day of September 1981

[SEAL]

Attest:

GERALD J. MOSSINGHOFF

Attesting Officer        Commissioner of Patents and Trademarks